United States Patent
Meetz et al.

(10) Patent No.: US 9,757,083 B2
(45) Date of Patent: Sep. 12, 2017

(54) SCANNING METHOD AND SYSTEM

(75) Inventors: Kirsten Meetz, Hamburg (DE); Ingwer Curt Carlsen, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1787 days.

(21) Appl. No.: 12/809,080

(22) PCT Filed: Dec. 26, 2008

(86) PCT No.: PCT/IB2008/055540
§ 371 (c)(1),
(2), (4) Date: Aug. 31, 2010

(87) PCT Pub. No.: WO2009/083921
PCT Pub. Date: Jul. 9, 2009

(65) Prior Publication Data
US 2010/0316279 A1 Dec. 16, 2010

(30) Foreign Application Priority Data
Dec. 28, 2007 (CN) .......................... 2007 1 0306620

(51) Int. Cl.
*A61B 6/00* (2006.01)
(52) U.S. Cl.
CPC .............. *A61B 6/504* (2013.01); *A61B 6/501* (2013.01)
(58) Field of Classification Search
CPC .......... A61B 6/032; A61B 6/504; A61B 6/507
USPC ....................................................... 382/131
See application file for complete search history.

(56) References Cited

U.S. PATENT DOCUMENTS

| 5,552,605 | A  | * | 9/1996  | Arata ................... G01T 1/1648 250/363.04 |
|---|---|---|---|---|
| 6,792,302 | B2 |   | 9/2004  | Wintermark et al. |
| 7,218,702 | B2 |   | 5/2007  | Mistretta et al. |
| 2005/0058331 | A1 |   | 3/2005  | Klotz |
| 2006/0262147 | A1 | * | 11/2006 | Kimpe ..................... G09G 3/20 345/690 |
| 2006/0274928 | A1 |   | 12/2006 | Collins et al. |

(Continued)

FOREIGN PATENT DOCUMENTS

EP          1709907 A1     10/2006
WO    WO2007/063442 A1 *  6/2007 ............. G06T 17/40

OTHER PUBLICATIONS

Camargo et al., Neuroimaging of Ischemia and Infarction, Apr. 2005, NeuroRx: The Journal of the American Society for Experimental NeuroTherapeutics, vol. 2, pp. 265-276.*

(Continued)

*Primary Examiner* — Joy Chng

(57) ABSTRACT

To improve the scanning effect, a scanning method is provided, which comprises the steps of performing at least one of an nCT scan and a CTA scan on an object so as to obtain a set of images; detecting characteristics of a region of interest based on the set of images; and performing a CTP scan on the region of interest by adopting the characteristics to obtain a CTP image. By deriving the characteristics of the region of interest, e.g. a lesion or an area covering the lesion, before performing the CTP scan, and by adapting the subsequent CTP scan based on the characteristics of the region of interest, the drawback introduced by a limited scan area of the CTP scanner is mitigated, or even overcome.

17 Claims, 2 Drawing Sheets

(56) References Cited

U.S. PATENT DOCUMENTS

| | | | | |
|---|---|---|---|---|
| 2007/0019846 A1* | 1/2007 | Bullitt | ............ | G06T 7/0014 |
| | | | | 382/128 |
| 2007/0098134 A1* | 5/2007 | Toyoshima | ............ | A61B 6/032 |
| | | | | 378/4 |
| 2008/0118139 A1* | 5/2008 | Huo | ............ | G06T 5/009 |
| | | | | 382/132 |
| 2008/0188962 A1* | 8/2008 | Suryanarayanan | .. | G06K 9/4638 |
| | | | | 700/89 |
| 2008/0212862 A1* | 9/2008 | Haras | ............ | A61B 5/4244 |
| | | | | 382/131 |

OTHER PUBLICATIONS

DICOM Supplement 73: Spatial Registration Storage SOP Classes, DICOM Standards Committee, Jan. 29, 2004, pp. 1-46.*

Camargo et al., Neuroimaging of Ischemia and Infarction, Apr. 2005, NeuroRx: The Journal of the American Society for Experimental NeuroTherapeutics, vol. 2, pp. 265-276.*

J. Eastwood et al "Perfusion CT With Iodinated Contrast Material" American Journal of Radiology, vol. 180, Jan. 2003 (Jan. 2003), pp. 3-12.

B. F. Tomandl et al "Comprehensive Imaging of Ischemic Stroke With Multisection CT" Radiographics, IL, Education Exhibit vol. 23, No. 3, May 1, 2003 (May 1, 2003), pp. 565-592.

M. Wintermark et al "Comparative Overview of Brain Perfusion Imaging Techniques" Stroke, vol. 36, 2005, pp. E83-E99.

M. Wintermark et al "Vasospasm After Subarachnoid Hemorrhage: Utility of Perfusion CT and CT Angiography on Diagnosis and Management" Original Research; Wintermark | AJNR | Jan. 27, 2005. www.ajnr.org; pp. 26-34.

R.G. Gonzalez Imaging-Guided Acute Ischemic Stroke Therapy From "Time Is Brani " to "Physiology is Brain" Apr. 2006 pp. 728-734.

A Srinivasan et al "State-Of-The-Art Imaging of Acute Stroke" Radiographics, vol. 26, 2006, pp. S75-S95, XP002526a83abstract, table 3 p. S77, col. S83.

* cited by examiner

SCANNING METHOD AND SYSTEM

FIELD OF THE INVENTION

The present invention relates to a scanning method and system, particularly a CT (Computed Tomography) scanning system.

BACKGROUND OF THE INVENTION

Thrombolysis is a very effective therapy for stroke patients. Instead of limiting thrombolysis within three hours after the onset of a stroke symptom, it is observed that, based on the patient's individual status, the time window of applying thrombolysis can be extended to 6 or 9 hours. This observation underscores the shift from the old concept of "Time is Brain" to the new concept of "Physiology is Brain".

In current practice, the following protocols are widely used in the case of multi-protocol CT imaging. FIG. 1 shows the steps of a multi-protocol CT scan. First, in step S110, an nCT (native CT) is performed to check whether a hemorrhagic stroke exists; if this hemorrhagic stroke does not exist, a CTP (CT perfusion) scan is performed in step S120 to determine the physiological parameters. Then, in step S125, a saline flash is optionally performed to clean the vascular system so as to prevent the influence of a previously applied contrast agent. In step S130, a CTA (CT angiography) can be performed to determine the status of the vessels and detect the clot that causes the ischemic stroke. It is possible to change the sequence between CTP and CTA after performing nCT. In current practice, the operation of CTP is the same, no matter whether it is performed before or after CTA.

However, CTP has the drawback that it is limited to a small portion of the brain. Currently, only two or four slices of the head are acquired at a standardized position that covers the territory of the MCA (mid cerebral artery). Although most ischemic stroke lesions (about 75%) can be found in the MAC territory, about 25% of the ischemic strokes are missed from the outset.

To extend CTP to the whole brain, a method named "Neuron Perfused Blood Volume Imaging" is proposed. This method extends the spatial coverage by reducing the number of time points to exactly two, which reduce the imaging resolution. The method is still in its testing phase. Another drawback of this method is its low image resolution.

SUMMARY OF THE INVENTION

It is an object, according to one embodiment of the present invention, to improve the method and system of CT scanning.

In a first aspect, according to one embodiment of the present invention, a method of scanning an object comprises the steps of: performing at least one of an nCT scan and a CTA scan on an object so as to obtain a set of images; detecting characteristics of a region of interest based on the set of images; and performing a CTP scan on the region of interest by adopting the characteristics to obtain a CTP image.

A region of interest, such as a lesion or an area comprising the lesion, is detected by applying the detection step to the set of images, e.g. an nCT image and/or a CTA image. Use of characteristics of this region of interest in the subsequent CTP scan as input parameter(s) provides the advantage that the CTP scan is performed in an appropriate field of view, i.e. in the region covering the lesion. More specifically, the relevant parts of the object, e.g. the brain, will be imaged. It is an advantage to mitigate or even overcome the influence of limited scan coverage of the CTP scan on the multi-protocol CT scan, and/or improve the scan accuracy to detect the potential clots, especially those outside the MCA territory. Furthermore, there is another advantage over the method of "Neuron Perfused Blood Volume Imaging" in that there is no need for a whole-brain CTP scanner, which saves costs and does not suffer from a low image resolution.

Optionally, when the set of images comprises at least one nCT image and one CTA image, which means that an nCT scan and a CTA scan are performed, a registration on the nCT image and the CTA image is performed during the detection step so as to obtain a spatial correlation, which can be further used to detect the region of interest, e.g. the lesion.

In other embodiments, automatic image-processing methods without user interaction are also provided, including applying grey value and pattern-based processing on the nCT image, and/or applying vessel tree extraction and analysis on the CTA image, so as to detect the region of interest. This provides the advantage that the image is processed without the need of user interaction to which current image-processing algorithms and methods are applicable.

In other embodiments, the physician's experience can be incorporated in the detection of the region of interest by presenting part or whole of the set of images, e.g. the nCT image and/or the CTA image, through a user interface and receiving input information through the user interface or another interface. The input information may indicate the possible location of the lesion, based on the physician's visual analysis. Advantageously, the input information can be obtained on the basis of combination and comparison of the nCT image and the CTA image.

In other embodiments, the computer-based image-processing and manual input can be combined. This method, referred to as semi-automatic image-processing, is advantageous because it does not only take the experience of physicians into account, but also advanced image-processing technologies.

In a second aspect, according to one embodiment of the invention, a scanning system comprises: a processor configured to detect characteristics of a region of interest comprised in a scan object, based on at least one of an nCT image and a CTA image; and a scanner configured to perform a CTP scan on the region of interest.

Use of this scanning system has the advantage that the region of interest, e.g. a lesion or an area covering the lesion, is located and that the characteristic or characteristics of the region of interest are utilized to locate the CTP scan area. Furthermore, while keeping the current high image resolution, there is no need to update the CTP scanner to a whole-brain CTP scanner.

In one embodiment, the characteristic or characteristics of the region of interest comprise at least one of location, quantity, size and extension of the region of interest.

Optionally, according to one embodiment, the scanner is further configured to perform an nCT scan and a CTA scan. In this situation, the scanner can be referred to as multi-protocol CT scanner.

According to one embodiment, the processor comprises a registration unit configured to register the nCT image and the CTA image so as to establish a spatial correlation between the CTA image and the nCT image. The spatial correlation is useful in improving the detection of the region of interest, i.e. the lesion.

Optionally, an nCT scanner and a CTA scanner are incorporated in this scanning system. It is also possible to only utilize nCT images and CTA images obtained from other scan systems.

To facilitate intervention by physicians, the lesion-based system optionally provides a user interface configured to present the nCT image and the CTA image and to receive input information indicating the suspected area in which the lesion is possibly located. The physician's experience is taken into consideration during detection of the lesion.

To overcome the influence introduced by a patient's movement during scanning, a motion correction processor is optionally incorporated in the scanning system in one embodiment of the present invention. The motion correction processor is configured to perform motion correction on the CTP image so as to mitigate movement of the patient during a CTP scan. In the system having an nCT scanner and a CTA scanner, the motion correction processor is further configured to perform motion correction on the nCT image and the CTA image.

A drawback of the current CTP scanner is its limited scan coverage. In current practice, the CTP scan is performed on the same area, i.e. the MCA territory, irrespective of the sequence of a CTP scan and a CTA scan. This may introduce the loss of some potential clots, which are located outside the MCA. The basic idea of the invention is that, before performing the CTP scan, the characteristics of the region of interest are detected, and the detected information is used as the scan parameter so as to help the CTP scanner to scan the interested area which might comprise a lesion, instead of merely scan the MCA territory. The influence of a limited scan area of the CTP scanner on the multi-protocol CT scanning method can thus be mitigated, or even overcome.

These and other aspects, features and/or advantages of the invention are apparent from and will be elucidated with reference to the embodiments described hereinafter.

BRIEF DESCRIPTION OF THE DRAWINGS

In these drawings, identical or similar reference numerals denote the same or similar functions/apparatuses.

DESCRIPTION OF EMBODIMENTS

Figure 1:
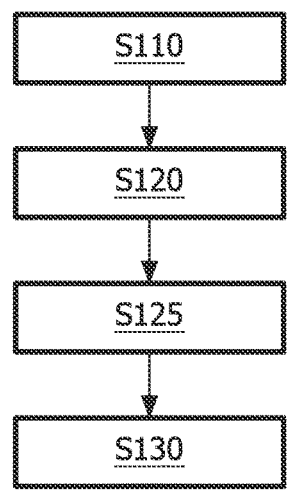
FIG. 1 is a flowchart of a known multi-protocol CT scan.
Figure 2:
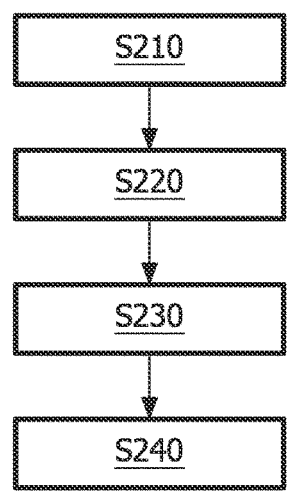
FIG. 2 is a flowchart, according to one embodiment of the present invention, of a lesion-based scan method.

According to one embodiment, FIG. 2 shows a method of first detecting a region of interest (e.g. a lesion/stroke area, such as a clot) and subsequently performing a CTP scan on the detected region of interest. In the method 200, nCT is performed first, in step S210, so as to judge whether the current stroke is a hemorrhagic stroke, which requires a different therapy. If there is no hemorrhagic stroke, a CTA scan is performed in step S220 so as to generate a CTA image, which may be a 3D image including vessel trees. Step S220 may be optional if the output of S210, i.e. the nCT image, is enough to ascertain the location/size/extension of a lesion. In step S230, detection is performed to detect the lesion, based on at least one of the nCT image and CTA image. As a result, the output of S230 should include at least one characteristic of the region of interest, e.g. location, size, extension, quantity, or any other parameter that can be used to represent a lesion. In step S240, the characteristic of the region of interest is used as a scan parameter to help the CTP scanner to scan the region of interest, which may cover the lesion.

In one preferred embodiment, it is advantageous to use the combination of nCT image and CTA image to detect the region of interest. Since the nCT image and the CTA image can provide different information, the combination may provide more extensive and accurate information about the lesion. To this end, in one embodiment, a registration is performed on the nCT image and the CTA image so as to establish a spatial correlation. The registration can adopt any currently available registration method, such as rigid registration techniques and mutual information-based registration techniques. The spatial correlation is useful in improving the accuracy when detecting the region of interest.

Figure 3:
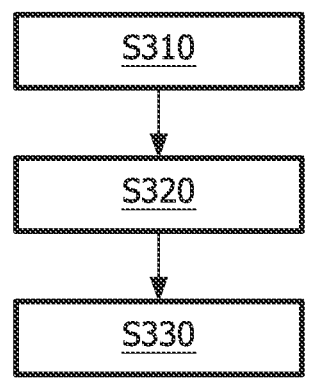
FIG. 3 is the flowchart of an image-processing method based on the combination of nCT and CTA images, according to one embodiment of the present invention.

FIG. 3 is a detailed flowchart of an embodiment of an image-processing method using the registration technique. In the method 300, the nCT image and the CTA image are registered so as to establish a spatial correlation between these two images in step S310. In step S320, the size, location and/or extension of the lesion can be detected. Different methods can be used in this step. For example, in automatic methods, grey value and pattern-based approaches can be applied to the nCT image and, if necessary, vessel tree extraction and analysis approaches can be applied to the CTA image. Other methods applicable to segment the combination of nCT and CTA images can also be used.

Alternatively, the physician's experience is taken into account. It is advantageous to present the nCT image and/or the CTA image to the physician through a user interface. The physician can use his expertise and/or other methods/apparatuses to judge the location and/or size of the lesion. It is also practical for the physician to only indicate a special area in which he thinks the lesion may be located. The physician's opinion can be received through the user interface or another user interface, and may be used as a scan parameter for the CTP scanner to perform a subsequent CTP scan.

It is also practical to combine the physician's experience and the advantages of image-processing methods. For example, the physician can indicate the suspected area and use the image-processing method to pay more attention to the indicated area. In other embodiments, the image-processing method may present some suspected areas, and the physician can select one or more areas based on his experience. The selected areas can be used as input parameters for CTP scanning.

It is also practical to perform a lesion detection based on user input, e.g. a region growth starting from a user-defined seed point. To this end, the size and/or extension of the lesion is calculated in step S330. The extension is useful because the affected brain tissue may include some irrecoverably damaged tissue, affected but still recoverable tissue, and unaffected tissue. Physicians can specify a territory around the lesion manually. Alternatively, a specific area including the lesion detection based on automatic methods can be selected as a scan area. It is also practical to combine the physician's input and image-process algorithms. It is advantageous to enable the physician to correct the selected scan area.

Figure 4:
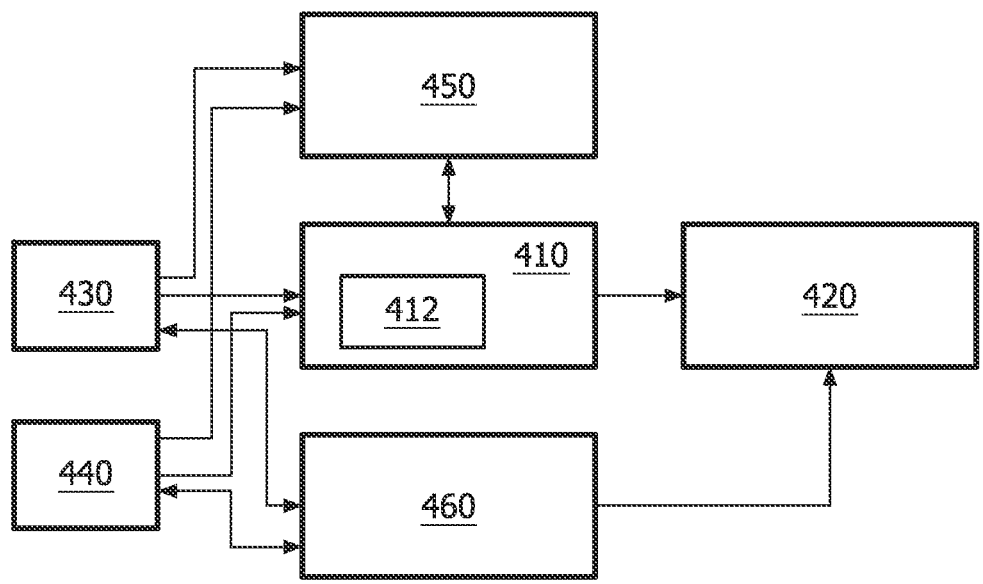
FIG. 4 is a block diagram of a scanning system according to one embodiment of the present invention.

FIG. 4 shows a scanning system for performing the lesion-based scanning method proposed above. The scanning system 400 comprises a processor 410 and a CTP scanner 420. The processor 410 is configured to detect characteristics of a region of interest of a scan object, based on at least one of an nCT image and a CTA image. The CTP scanner 420 is configured to perform a CTP scan on the region of interest by adopting the characteristics of this region of interest.

Optionally, the processor 410 may include a registration unit 412 for registering the nCT image and the CTA image so as to obtain a spatial correlation.

In one embodiment, the processor can have the capability to perform grey value and pattern-based methods on the nCT image, and/or vessel tree extraction and analysis on the CTA image.

The lesion-based scan system may further incorporate an nCT scanner 430 and/or a CTA scanner 440. The nCT scanner 430 performs an nCT scan on the scan object so as to generate an nCT image, and the CTA scanner 440 performs a CTA scan on the scan object so as to generate a CTA image. The nCT image and the CTA image can also be output from other scan systems and are re-usable in the lesion-based scanning system 400.

To facilitate intervention by physicians, the system 400 further includes a user interface 450. The user interface 450 has the basic function of receiving input information from the physician/operator, indicating at least one of location, size and extension of the suspected lesion. The user interface 450 can also be configured to present at least one of the nCT image and the CTA image to the physician/operator.

In practice, a patient always moves during scanning. The lesion-based scanning system 400 may further comprise a motion correction processor 460 which is configured to perform motion correction on the CTP image so as to mitigate movement of the patient during a CTP scan. For the system including nCT scanner 430 and CTA scanner 440, the motion correction processor 460 may be further configured to correct the patient's movement during the nCT/CTA scan.

This embodiment has the advantage of helping the CTP scanner in scanning a suspected area instead of the central brain. Moreover, there is no need to extend the CTP scan to the whole brain, which may be expensive and provides a low image resolution.

The embodiment of FIG. 4 shows three CT scanners, including one nCT scanner 430, one CTA scanner 440, and one CTP scanner 420. Alternatively, one multi-protocol scanner can perform the functions of nCT scanning, CTA scanning and CTP scanning, and can be incorporated in a single CT scanner, referred to as multi-protocol scanner.

The invention can be implemented in any suitable form including hardware, software, firmware or any combination of these. The invention or some of its features can be implemented as computer software. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described with reference to the specified embodiments, it is not intended to be limited to the specific form set forth herein. Rather, the scope of the present invention is limited only by the accompanying claims. In the claims, use of the verb "comprise" and its conjugations does not exclude the presence of other elements or steps. Although individual features may be included in different claims, these may possibly be advantageously combined, and the inclusion in different claims does not imply that a combination of features is not feasible and/or advantageous. In addition, singular references do not exclude a plurality. Furthermore, reference signs in the claims shall not be construed as limiting the scope.

The invention claimed is:

1. A method of scanning an object, the method comprising the steps of:
   a) performing a native CT (nCT) scan and a CTA scan with a CT scanner on the object to obtain a set of images, wherein the performing at least one of the nCT scan and the CTA scan further comprises:
      performing the nCT scan with the CT scanner on the object to obtain an nCT image; and
      performing the CTA scan with the CT scanner on the object to obtain a CTA image;
      wherein the set of images includes the nCT image and the CTA image;
   b) detecting, via a configured hardware processor, characteristics of a region of interest based on the set of images, wherein the detecting further comprises:
      performing a registration on the nCT image and the CTA image to establish a spatial correlation; and
      detecting the characteristics of the region of interest based on the spatial correlation between the registered nCT image and the CTA image; and
   c) performing a CTP scan on the region of interest with the CT scanner by adopting the detected characteristics as at least one scan parameter to obtain a CTP image.

2. The method as claimed in claim 1, wherein the detecting, via the hardware processor, characteristics of the region of interest based on the set of images further comprises detecting at least one of location, quantity, size and extension of the region of interest; and wherein the region of interest includes at least one lesion.

3. The method as claimed in claim 1, wherein the detecting, via the hardware processor, characteristics of the region of interest based on the set of images further comprises applying grey value and pattern-based processing on the nCT image of the set of images so as to detect the region of interest.

4. The method as claimed in claim 1, wherein the detecting, via the hardware processor, characteristics of the region of interest based on the set of images further comprises the step of applying vessel tree extraction and analysis on the CTA image of the set of images so as to detect the region of interest.

5. The method as claimed in claim 1, wherein the detecting, via the hardware processor, characteristics of the region of interest based on the set of images further comprises:
   presenting the set of images through a user interface; and
   receiving input information through the user interface, the input information characterizing the region of interest.

6. The method as claimed in claim 1, wherein detecting comprises performing image-processing on the spatially correlated nCT and CTA images so as to detect the region of interest with input information received through a user interface.

7. The method as claimed in claim 5, wherein the input information is generated on a basis of the set of images and comprises a location of the region of interest.

8. The method as claimed in claim 1, wherein the object is at least one of a cerebellum and a cerebrum.

9. The method as claimed in claim 1, wherein the region of interest comprises a lesion.

10. The method as claimed in claim 1, further comprising a step of performing motion correction on at least one of the nCT image, the CTA image and the CTP image.

11. A scanning system comprising:
a processor configured to detect characteristics of a region of interest comprised in a scanned object on a basis of a native CT (nCT) image and a CTA image;
a registration unit configured to register the nCT image and the CTA image to establish a spatial correlation between the CTA image and the nCT image; and
a CT scanner configured to perform a CTP scan on the region of interest using the detected characteristics spatially correlated as at least one scan parameter.

12. The scanning system as claimed in claim 11, wherein the characteristics of the region of interest comprise at least one of location, quantity, size and extension of the region of interest; and wherein the region of interest includes at least one lesion.

13. The scanning system as claimed in claim 11, wherein the scanner is further configured to perform an nCT scan and a CTA scan.

14. The scanning system as claimed in claim 11, further comprising:
an nCT scanner configured to perform an nCT scan on the scan object so as to obtain the nCT image;
a CTA scanner configured to perform a CTA scan on the scan object so as to obtain the CTA image; and
wherein the at least one scan parameter includes a non-mid cerebral artery location.

15. The scanning system as claimed in claim 11, wherein the processor is further configured to perform at least one of a grey value and pattern-based method on the nCT image, and vessel tree extraction and analysis on the CTA image, and the extracted vessel tree is spatially correlated to the nCT image.

16. The scanning system as claimed in claim 11, further comprising: a user interface configured to receive input information indicating a location of the region of interest, wherein the processor adopts the input information so as to detect the characteristics of the region of interest.

17. The scanning system as claimed in claim 11, further comprising: a motion correction processor configured to perform motion correction on the at least one of the nCT image, the CTA image, and a CTP image from the CTP scan.

* * * * *